(12) United States Patent
Lambert et al.

(10) Patent No.: US 6,452,057 B1
(45) Date of Patent: Sep. 17, 2002

(54) PROCESS FOR PREPARING HALOHYDROCARBONS IN THE PRESENCE OF A CO-CATALYST

(75) Inventors: Alain Lambert, Beauvechain; Véronique Mathieu, Wavre, both of (BE); Charles-Marie Anciaux, Tavaux (FR)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/677,125

(22) Filed: Sep. 29, 2000

(30) Foreign Application Priority Data

Oct. 6, 1999  (EP) .............................. 99203265

(51) Int. Cl.⁷ .......................... C07C 21/18; C07C 17/08
(52) U.S. Cl. ................ 570/172; 570/164; 570/165; 570/166; 570/162; 570/168; 570/169
(58) Field of Search ................ 570/172, 164, 570/165, 166, 167, 168, 169

(56) References Cited

U.S. PATENT DOCUMENTS

| | | | |
|---|---|---|---|
| 3,268,603 A | 8/1966 | Scherling | 570/257 |
| 3,454,657 A | 7/1969 | Decker et al. | 260/651 |
| 3,649,698 A | 3/1972 | Goble et al. | 570/257 |
| 3,651,019 A | 3/1972 | Asscher et al. | 260/77.2 |
| 3,862,978 A | 1/1975 | Decker et al. | 260/465.7 |
| 5,446,217 A | 8/1995 | Van Der Puy et al. | 570/156 |
| 5,792,893 A | 8/1998 | Wilson et al. | 570/257 |
| 5,917,098 A | 6/1999 | Bertocchio et al. | 570/164 |

FOREIGN PATENT DOCUMENTS

| | | |
|---|---|---|
| EP | 0 729 932 | 4/1996 |
| EP | 787 707 | 8/1997 |
| FR | 1288511 | 5/1961 |
| GB | 1146463 | 3/1969 |
| SA | 98/3775 | 1/2000 |
| SA | 98/3781 | 1/2000 |
| WO | 95/04022 | 2/1995 |
| WO | 97/05089 | 2/1997 |
| WO | 97/07083 | 2/1997 |
| WO | 97/15540 | 5/1997 |
| WO | 98/50329 | 11/1998 |
| WO | 98/50330 | 11/1998 |

OTHER PUBLICATIONS

Kotora et al., "Addition of Tetrachloromethane to Halogenated Ethenes Catalyzed by Transition Metal Complexes," *Journal of Meolecular Catalysts*, 77:51–60 (1992).

Ullmann's Encyclopedia of Industrial Chemistry, 1992, vol. B4, pp. 387–388.

Asscher and Vofsi, *Chlorine Activation by Redox Transfer. Part II. The addition of Carbon Tetrachloride to Olefins*, 1963, pp. 1887–1896.

R. Freidlinda et al., "Telomerization of 2–Chloropropene with Carbon Tetrachloride", Bull. Acad. Sci. USSR, 28, pp. 1766–1769(1979).

Kotora et al., "Selective Additions of Polyhalogenate Compounds to Chloro Substituted Ethenes Catalyzed by a Copper Complex", React. Kinet. Catal, Lett. 44, No. 2, pp. 415–419 (1991).

*Primary Examiner*—Alan Siegel
(74) *Attorney, Agent, or Firm*—Connolly Bove Lodge & Hutz LLP

(57) ABSTRACT

Halohydrocarbons comprising at least 3 carbon atoms are obtained by batchwise reaction between a haloalkane and an olefin in the presence of a catalyst and a co-catalyst. The addition of at least some of the co-catalyst is carried out gradually. At least some of the co-catalyst is recovered with a view to its re-use.

12 Claims, No Drawings

PROCESS FOR PREPARING HALOHYDROCARBONS IN THE PRESENCE OF A CO-CATALYST

The present invention relates to a process for preparing halohydrocarbons comprising at least 3 carbon atoms, by catalytic reaction between a haloalkane and an olefin.

The addition of a haloalkane to an olefin is a well-known reaction. However, it is occasionally difficult to control the reaction such that only one olefin molecule adds to one haloalkane molecule (formation of a 1:1 addition product or adduct).

Patent application WO 97/07083 discloses a process for preparing halohydrocarbons under the catalytic action of cuprous chloride in the presence of t-butylamine as co-catalyst. Patent application EP-A-787 707 discloses a process for preparing 1,1,1,3,3-pentachlorobutane under the catalytic action of cuprous chloride in the presence of co-catalysts of amine type. In such processes, the various constituents of the reaction medium are first introduced into a reactor which is then brought to the reaction temperature. However, the yield of and selectivity towards telomerization product are unsatisfactory. Furthermore, considerable, or even total, losses of co-catalyst are observed therein due to spurious degradation reactions in the reaction medium.

The invention is consequently directed towards providing a process which gives access, in excellent yields and selectivities, to halohydrocarbons comprising at least 3 carbon atoms, in a single step starting with readily accessible reagents and in which the losses of co-catalyst are minimized, thus allowing maximum re-use.

Consequently, the present invention relates to batchwise process for preparing halohydrocarbons comprising at least 3 carbon atoms, according to which haloalkane and an olefin are reacted, in a reaction medium, in the presence of a catalyst and a co-catalyst, in which process
a) in a first step, at least some of the co-catalyst is gradually added to the reaction medium during the reaction;
b) in a subsequent step, at least some of the co-catalyst is recovered with a view to its re-use.

It has been found, surprisingly, that when a gradual addition to the reaction medium of at least some of the co-catalyst is carried out during the reaction, very little degradation of the co-catalyst is observed, while at the same time an excellent yield of halohydrocarbon is achieved. The process according to the invention also makes it possible to control the exothermicity of the reaction, which is a considerable advantage in an industrial-scale synthesis of halohydrocarbons.

In the process according to the invention, the initial reaction medium generally comprises the catalyst, the haloalkane, the olefin and optionally a solvent. The initial reaction medium also advantageously comprises a fraction of the co-catalyst. In this case, the fraction of the co-catalyst included in the initial reaction medium is generally at least 1% of the total amount of co-catalyst used. This fraction is often at least 5%. It is usually at least 10%. It is preferably at least 15%. It is generally not more than 80% of the total amount of co-catalyst. It is often not more than 70%. It is preferably not more than 60%.

The gradual addition can be carried out in the liquid phase or in the gas phase. The liquid-phase addition can be carried out, for example, by means of a tube dipping into the reaction medium. The gas-phase addition can be carried out, for example, by introducing the co-catalyst in vapour form into the reactor atmosphere.

The gradual addition of the co-catalyst can be, for example, an addition carried out in several portions, which may or may not be identical. This method of adding the co-catalyst corresponds to what is called, for bioreactors, a reaction of "fed-batch" type (Ullmann's Encyclopedia of Industrial Chemistry, 5th Ed. Vol. B4 pp. 387–388). Generally, a portion of co-catalyst is introduced into the initial reaction medium, and at least one other portion is then added subsequently, during the reaction. The number of portions to be used is theoretically not limited, thus approaching another mode of addition of the co-catalyst according to which the gradual addition is carried out continuously. However, a number of portions of not more than 100 is generally used. The number is often not more than 50. The number is usually not more than 20. A number of not more than 10 gives good results. A number of not more than 5 is advantageous. A number of not more than 4 is preferred. Excellent results are obtained with a number of 2 or 3.

The time intervals between the additions of the portions are generally at least 1 min. The intervals are often at least 5 min. The intervals are usually at least 30 min. The intervals are preferably at least 1 h. Intervals of about 2, 3, 4, 5 or 6 h give good results.

In another mode of addition of the co-catalyst in the process according to the invention, the gradual addition of at least some of the co-catalyst is carried out continuously. This mode of addition corresponds to what is called, for bioreactors, a reaction of "extended fed-batch" type (Ullmann's Encyclopedia of Industrial Chemistry, 5th Ed. Vol. B4 pp. 387–388). It is possible, for example, to introduce a portion of co-catalyst into the initial reaction medium, and then subsequently to add a desired amount of co-catalyst continuously during the reaction.

In this embodiment of the process according to the invention, the ratio between the molar flow rate of co-catalyst added continuously and the molar amount of catalyst used is called R and is defined by the following equation:

$$R = [\text{amount of co-catalyst/time}] \,(\text{mol/h})/\text{amount of catalyst per batch (mol)}.$$

The ratio R is generally at least $0.1 \text{ h}^{-1}$. The ratio is usually at least $0.5 \text{ h}^{-1}$. The ratio is preferably at least $1 \text{ h}^{-1}$. In a particularly preferred manner, the ratio is at least 2. In a most particularly preferred manner, the ratio is at least 3. The ratio is generally not more than $1000 \text{ h}^{-1}$. The ratio is often not more than $500 \text{ h}^{-1}$. The ratio is usually not more than $100 \text{ h}^{-1}$. The ratio is preferably not more than $50 \text{ h}^{-1}$. In a particularly preferred manner, the ratio is not more than 10. In a most particularly preferred manner, the ratio is not more than 9. The time over which the continuous addition is carried out is generally at least 10 min. The time is usually at least 30 min. The time is preferably at least 1 h. Times of about 2, 3, 4, 5 or 6 h give good results.

One particularly advantageous embodiment of the process consists in regulating the addition of the co-catalyst as a function of the temperature of the reaction medium.

In one variant of the process according to the invention, in addition to the gradual addition of the co-catalyst, at least some of the olefin is gradually added. In this variant, the initial reaction medium generally comprises the catalyst, the haloalkane and, optionally, solvent. The initial reaction medium also advantageously comprises co-catalyst and/or olefin. It has been found, surprisingly, that when at least some of the co-catalyst and at least some of the olefin are added gradually, in addition to the advantages mentioned above, an increase is observed in the selectivity towards halohydrocarbons derived from the addition of one molecule of haloalkane to one molecule of olefin.

The gradual addition of the olefin can be carried out separately from the gradual addition of the co-catalyst. A gradual addition of a mixture of olefin and co-catalyst can also be carried out.

In another variant of the process according to the invention, in addition to the gradual addition of at least some of the co-catalyst or of at least some of the co-catalyst and of at least some of the olefin, a gradual addition of at least some of the haloalkane is carried out. In this variant, the initial reaction medium generally comprises the catalyst and, optionally, solvent. The initial reaction medium also advantageously comprises co-catalyst and/or haloalkane. The initial reaction medium can also comprise olefin. The gradual addition of the haloalkane can be carried out separately from the gradual addition of the co-catalyst and optionally of the olefin. A gradual addition of a mixture of haloalkane and co-catalyst can also be carried out. A gradual addition of a mixture comprising co-catalyst, haloalkane and olefin is preferably carried out.

A gradual addition to the reaction medium of other compounds to be used in the reaction such as, for example, the catalyst and the solvent, can also be carried out. The specific modes and conditions of gradual addition described above with regard to the co-catalyst also apply, where appropriate, to the gradual addition of the olefin, haloalkane and/or any other compound which is added gradually.

In general, after the end of the gradual addition, the reaction medium is left to react for a further amount of time which is sufficient to obtain an optimum between the conversion of the olefin and the observed degradation of the co-catalyst.

In the process according to the invention, the catalyst can be chosen from the metal derivatives known to catalyse the reaction of a haloalkane with an olefin. Copper salts and organocopper compounds are particularly preferred as catalyst. Such catalysts are described, for example, in patent applications WO-A-98/50329 which corresponds to U.S. Ser. No. 09/423,258, and WO-A-98/50330 which corresponds to U.S. Ser. No. 09/422,199 the content of which are incorporated by reference into the present application. Copper (I) chloride, copper (II) chloride, in anhydrous or dihydrate form, or copper (II) acetylacetonate give good results. Anhydrous copper (II) chloride is particularly preferred.

In the process according to the invention, the reaction is carried out in the presence of a co-catalyst selected, for example, from the group consisting of amines and trialkylphosphine oxides. An amine is preferably used as co-catalyst, preferably isopropylamine, t-butylamine and the tert-alkyl amines Primene® 81-R and JM-T sold by Rohm & Haas Company. t-Butylamine and the amines Primene® 81-R and Primene® JM-T are most particularly preferred. The amine Primene® 81-R is a mixture of primary and tert-alkyl amines containing from 12 to 14 carbon atoms. The amine Primene® JM-T is a mixture of primary and tert-alkyl amines containing from 18 to 22 carbon atoms.

Among the trialkylphosphine oxides which can be used as co-catalyst, mention may be made in particular of the compounds of formula (R1R2R3)PO, in which R1, R2 and R3 represents identical or different, preferably linear C3–C10 alkyl groups. Tri(n-butyl)phosphine oxide, tri(n-hexyl)phosphine oxide, tri(n-octyl)-phosphine oxide, n-octyldi(n-hexyl)phosphine oxide and n-hexyldi(n-octyl) phosphine oxide and mixtures thereof are particularly selected.

A catalyst/co-catalyst system which is preferred in the process according to the invention is the system consisting of a copper compound and an amine. Catalyst/co-catalyst systems formed from copper (II) acetylacetonate or copper (II) chloride with t-butylamine are particularly preferred.

Another catalyst/co-catalyst system which is most particularly preferred is the system formed from copper (II) acetylacetonate and Primene® JM-T.

The haloalkanes used in the process according to the present invention preferably contain from 1 to 3 carbon atoms and at least two chlorine atoms. Examples of haloalkanes according to the present invention which may be mentioned include dichloromethane, chloroform, carbon tetrachloride and 1,1,1-trichloroethane. Carbon tetrachloride is most particularly preferred. The haloalkanes can also comprise other substituents such as other halogen atoms, alkyl groups or haloalkyl groups. However, haloalkanes containing only chlorine as halogen are preferred.

The olefin used in the process according to the present invention is generally an ethylene, a propylene or a butene, optionally substituted with a substituent. Haloolefins are particularly suitable for use. Among the haloolefins, chloroolefins give good results. Chloroolefins which can be used in the process according to the invention generally correspond to the general formula

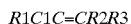  (I)

in which R1, R2, R3 and R4 independently represent an H or Cl atom, a linear, cyclic or branched, optionally substituted alkyl or alkenyl group, or an optionally substituted aryl or heteroaryl group. Non-limiting examples of chloroolefins which may be mentioned include vinyl chloride, vinylidene chloride, trichloroethylene and various chloropropene isomers such as 1-chloro-1-propene, 2-chloro-1-propene and 3-chloro-1-propene. Excellent results can be obtained with vinyl chloride and 2-chloro-1-propene.

The overall molar ratio, i.e. between the total amounts used per batch, between the catalyst and the olefin is usually greater than or equal to 0.0001. It is advantageously greater than or equal to 0.0005. It is preferably greater than or equal to 0.001. The molar ratio between the catalyst and the olefin is usually less than or equal to 1. It is advantageously less than or equal to 0.5. It is preferably less than or equal to 0.1.

The amount of co-catalyst used per batch, expressed on a molar basis, is generally at least 10 times the amount of catalyst used per batch. The amount of co-catalyst used is preferably at least 20 times the amount of catalyst. The amount is generally not more than 100 times the amount of catalyst. The amount is preferably not more than 75 times the amount of catalyst.

The recovery of the co-catalyst in step (b) of the process according to the invention can be carried out by well-known separation techniques. It is also advantageously possible to use a method for recovering a co-catalyst from an aqueous phase, comprising a step of treating an aqueous phase with at least one base and a step in which the co-catalyst is isolated from the aqueous phase treated with washing. The aqueous phase can be obtained, for example, by placing the reaction medium containing co-catalyst, obtained after step (a) of the process according to the invention, in contact with an aqueous medium, preferably with a hydrochloric acid solution.

The reaction medium is kept at a temperature and pressure that are sufficient to allow the catalytic reaction of the haloalkane with the olefin. The reaction conditions that are preferred in the process according to the invention as regards the temperature, pressure and time are described in patent application WO-A-98/50330 which corresponds to U.S. Ser. No. 09/422,199, the content of which is incorporated by reference into the present application. This is likewise the case for the molar ratios between the haloalkane and the olefin, between the co-catalyst and the olefin and, where appropriate, between the solvent and the olefin, it being understood that these are ratios between the overall amounts used.

In the process according to the invention, the presence of a co-catalyst generally makes it possible to carry out the reaction in the absence of solvent. However, the reaction can also be carried out in the presence of a solvent. Any solvent in which the reagents form the desired product in satisfactory yield an be used.

The halohydrocarbons obtained according to the process of the present invention generally belong to the family of chloroalkanes comprising at least three carbon atoms. The halohydrocarbons often contain only chlorine as halogen.

The halohydrocarbons obtained according to the process of the present invention preferably correspond to the general formula $C_nH_{(2n+2)-p}Cl_p$, in which n is an integer and takes the values 3 or 4 and p is an integer which takes the values 3 to 7. Examples of compounds obtained according to the process of the present invention are 1,1,1,3,3-pentachloropropane, 1,1,2,3,3-pentachloropropane, 1,1,1,3,3-pentachlorobutane, 1,1,1,3-tetrachloropropane, 1,1,3,3-tetrachlorobutane, 1,1,1,3,3,3-hexachloropropane and 1,1,-dichloro-2-trichloromethylpropane. Among these compounds, 1,1,1,3,3-pentachloropropane, 1,1,1,3,3-pentachlorobutane and 1,1,1,3,3,3-hexachloropropane are preferred. 1,1,1,3,3-Pentachlorobutane and 1,1,1,3,3-pentachloropropane are most particularly preferred.

The halohydrocarbons obtained according to the process of the invention are precursors of the corresponding fluoro analogues, which can be readily obtained by treatment with hydrogen fluoride, which is preferably anhydrous, optionally in the presence of a fluorinating catalyst such as, for example, an antimony salt, a titanium salt, a tantalum salt or a tin salt. The halides are preferred as salts of the said metals. Other fluorinating catalysts which can be used are chosen from the compounds, preferably the oxides, of chromium, of aluminium and of zirconium. Specific examples of fluorohydrocarbons correspond to the formula $C_nH_{(2n+2)-p}F_p$, in which n is an integer and takes the values 3 or 4 and p is an integer which takes the values 3 to 7. Preferred fluorohydrocarbons are chosen from 1,1,1,3,3-pentafluoropropane, 1,1,1,3,3,3-hexafluoropropane and 1,1,1,3,3-pentafluorobutane.

The invention consequently also relates to a method for obtaining a fluorohydrocarbon, comprising (a) the synthesis of a halohydrocarbon according to the process according to the invention, and (b) a treatment of the halohydrocarbon obtained from (a) with hydrogen fluoride as described above.

The examples below are intended to illustrate the invention without, however, limiting it.

EXAMPLE 1

1,1,1,3,3-Pentachlorobutane (HCC-360) was prepared by reaction between 2-chloro-1-propene (2-CPe) and carbon tetrachloride in the presence of Cu(II) acetylacetonate and Primene® JM-T. To do this, 0.15 g of copper salt, 0.9 g of Primene® JM-T and 48 g of CC14 were introduced into a 300 ml hastelloy C276 autoclave. The apparatus was then closed hermetically and placed in a vertical oven. Stirring was provided by a magnetic bar placed in the bottom of the autoclave. The temperature was raised gradually. When it reached 90° C., a solution containing 54 g of 2-CPe, 168 g of $CCl_4$ and 5 g of Primene® JM-T was fed in continuously over a period of 4 h at a flow rate of 1 ml/min, to achieve $2CPe/CCl_4$/copper salt/amine overall molar ratios of 1/2.3/0.001/0.03. The temperature of the autoclave was then maintained at 90° C. for 3 h after the end of the introduction of the reagents. The autoclave was then allowed to cool. A sample of liquid was then taken by syringe and assayed by a chromatographic method. The conversion of the 2-CPe was 97% and the selectivity towards HCC-360 was 93.5%.

EXAMPLE 2

Comparative

Example 1 was repeated, introducing all of the reagents (2-CPe and $CCl_4$) and the co-catalyst (Primene® JM-T) at the start of the test. After reaction for 5 h, the conversion of the 2-CPe was 45%, with a selectivity towards HCC-360 of 81%.

EXAMPLE 3

1,1,1,3,3-pentachlorobutane was prepared by reaction between 2-chloro-1-propene (2-CPe) and carbon tetrachloride in the presence of cupric chloride and t-butylamine. To do this, 0.094 g of $CuCl_2$, 27.1 g of 2-CPe and 108.5 g of $CCl_4$ were introduced into a 300 ml hastelloy C276 autoclave. The apparatus was then closed hermetically and placed in a vertical oven. Stirring was provided by a magnetic bar placed in the bottom of the autoclave. The temperature was raised gradually. When it reached 70° C., 2.1 g of t-butylamine was fed in continuously over a period of 2 h, in order to achieve 2-CPe/$CCl_4$/$CuCl_2$/t-butylamine overall molar ratios of 1/2/0.002/0.08. After 10 h at 70° C., the conversion of the 2-CPe was 99% and the selectivity towards HCC-360 was 98.8%.

EXAMPLE 4

1,1,1,3,3-pentachlorobutane was prepared: by reaction between 2-chloro-1-propene (2-CPe) and carbon tetrachloride in the presence of cupric chloride in the presence of cupric chloride and t-butylamine. To do this, 0.093 g of $CuCl_2$, 8.8 g of 2-CPe, 106.9 g of $CCl_4$ and 0.7 g of t-butylamine were introduced into a 300 ml hastelloy C276 autoclave. The apparatus was then closed hermetically and placed in a vertical oven. Stirring was provided by a magnetic bar placed in the bottom of the autoclave. The temperature was raised gradually to 70° C. An additional 8.8 g of 2-CPe and 0.7 g of t-butylamine were introduced after reaction for 2 h and 5 h, in order to achieve 2-CPe/$CCl_4$/$CuCl_2$/t-butylamine overall molar ratios of 1/2/0.002/0.08. After 10 h at 70° C., the conversion of the 2-CPe was 100% and the selectivity towards HCC-360 was 97.5%. 74% of the t-butylamine was consumed.

EXAMPLE 5

Comparative with Examples 3 and 4

Examples 3 and 4 were repeated, introducing all of the reagents (2-CPe and $CCl_4$)and the co-catalyst (t-butylamine) at the start of the test. After reaction for 10 h at 70° C., the conversion of the 2-CPe was total (100%) but the selectivity towards HCC-360 was only 95.1%. 93% of the t-butylamine was consumed.

EXAMPLE 6

(Recovery of the t-butylamine)

A reaction for the manufacture of 1,1,1,3,3-pentachlorobutane was carried out according to the process according to the invention, using CuCl$_2$.2H$_2$O as catalyst and t-butylamine as co-catalyst. The reaction mixture obtained from this reaction was subjected to washing with an aqueous HCl solution containing 1.112 mol of HCl per kg, at a rate of 0.35 kg of aqueous HCl solution per kg of reaction mixture. After separation of the phases by settling, an organic phase was recovered, consisting essentially of 1,1,1,3,3-pentachlorobutane and of unconsumed reagents, with a copper content of 0.03 mg/kg and a t-butylamine content of 1.34 mmol/kg, and an aqueous phase containing 644 mg Cu/kg and 694 mmol of t-butylamine/kg. A fraction of the aqueous phase recovered was heated to the boiling point in distillation apparatus, while bringing the pH to a value of 10.5 by addition to the boiling aqueous phase of an aqueous solution with an NaOH content of 50% by weight. The equivalent of 96.2% of the t-butylamine used in the synthesis of the 1,1,1,3,3-pentachlorobutane was recovered by distillation, in a purity of 997.6 g of t-butylamine/kg. The water recovered after filtration contained only 3.8 mg/kg of Cu and 2.9 mmol/kg of t-butylamine.

What is claimed is:

1. Batchwise process for preparing halohydrocarbons comprising at least 3 carbon atoms, according to which a haloalkane and an olefin are reacted, in a reaction medium, in the presence of a catalyst and a co-catalyst, in which process
    a) in a first step, at least some of the co-catalyst is gradually added to the reaction medium during the reaction;
    b) in a subsequent step, at least some of the co-catalyst is recovered with a view to its re-use.

2. Process according to claimed 1, in which the addition is carried out in several portions.

3. Process according to claim 1, in which the addition is carried out continuously.

4. Process according to claim 1, in which a gradual addition of at least some of the olefin is also carried out.

5. Process according to claim 1, in which a gradual addition of at least some of the haloalkane is also carried out.

6. Process according to claim 1, in which the catalyst is a copper compound.

7. Process according to claim 1, in which the co-catalyst is an amine.

8. Process according to claim 1, in which the olefin is a haloolefin.

9. Process according to claim 8, in which the haloolefin is a chloroolefin corresponding to the general formula R1ClC=CR2R3 in which R1, R2 and R3 independently represent: H, Cl, linear, cyclic or branched, optionally substituted alkyl or alkenyl; optionally substituted aryl or heteroaryl.

10. Process according to claim 1, in which the halohydrocarbon prepared is 1,1,1,3,3-pentachloropropane; 1,1,2,3,3-pentachloropropane; 1,1,1,3,3-pentachlorobutane; 1,1,3,3-tetrachloropropane; 1,1,3,3-tetrachlorobutane; 1,1,1,3,3,3-hexachloropropane or 1,1-dichloro-2-trichloromethyl-propane.

11. Method for obtaining a fluorohydrocarbon, comprising
    a) the synthesis of a halohydrocarbon according to claim 1,
    b) a treatment of the halohydrocarbon obtained from a) with hydrogen fluoride.

12. A batchwise process for preparing halohydrocarbons comprising at least 3 carbon atoms, which comprises reacting a haloalkane and an olefin in a reaction medium, in the presence of a catalyst and a co-catalyst, in which the process has the following conditions:
    a) in a first step, at least some of the co-catalyst is gradually added to the reaction medium during the reaction;
    b) in a subsequent step, at least some of the co-catalyst is recovered.

* * * * *